US00PP36967P2

(12) United States Plant Patent
Scheffers

(10) Patent No.: US PP36,967 P2
(45) Date of Patent: Sep. 16, 2025

(54) ***DRACAENA* PLANT NAMED 'DRAHUR01'**

(50) Latin Name: *Dracaena fragrans*
Varietal Denomination: DRAHUR01

(71) Applicant: Ruud Scheffers, Honselersdijk (NL)

(72) Inventor: Ruud Scheffers, Honselersdijk (NL)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 18/831,363

(22) Filed: Dec. 12, 2024

(51) Int. Cl.
*A01H 5/12* (2018.01)
*A01H 6/12* (2018.01)

(52) U.S. Cl.
USPC ..... Plt./383
CPC ..... *A01H 6/12* (2018.05)

(58) Field of Classification Search
USPC ..... Plt./383
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Dracaena* plant named 'DRAHUR01' which is characterized by an abundance of lorate foliage that is slightly concave, curled under and spiraled, dark green foliage that is broadly striped with light yellow-green along the central portion of the lamina, foliage that is very narrowly margined with a translucent greyed-green, and the stability of these characteristics from generation to generation.

2 Drawing Sheets

Latin name of the genus and species: The Latin name of the genus and species of the novel variety disclosed herein is *Dracaena fragrans.*

Variety denomination: The inventive cultivar of *Dracaena* disclosed herein has been given the variety denomination 'DRAHUR01'.

BACKGROUND OF THE INVENTION

Parentage: 'DRAHUR01' is a naturally-occurring, whole-plant mutation of a *Dracaena fragrans* 'Kanzi' plant (U.S. Plant Pat. No. 12,691) which was discovered at a commercial greenhouse in Honselersdijk, the Netherlands in the spring of 2018. The mutation was initially noted for its abundant light green foliage with narrow greyed-green near translucent leaf margins. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'DRAHUR01' is accomplished by way of rooting stem cuttings. Propagation was first performed in July of 2018 at the inventor's commercial greenhouse in Honselersdijk, the Netherlands. Through five subsequent generations, the unique features of this cultivar have proven to be stable and true to type.

SUMMARY OF THE INVENTION

The cultivar 'DRAHUR01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRAHUR01'. These characteristics in combination distinguish 'DRAHUR01' as a new and distinct *Dracaena fragrans* cultivar:

1. *Dracaena* 'DRAHUR01' exhibits an abundance of lorate foliage born on an unbranched stem; and
2. *Dracaena* 'DRAHUR01' exhibits foliage that is slightly concaved, curled under, and spiraled; and
3. *Dracaena* 'DRAHUR01' exhibits dark green foliage that is broadly striped with light yellow-green along the central portion of the lamina, and very narrowly margined with a translucent greyed-green.

BOTANICAL DESCRIPTION OF THE PLANT

Figure 1:
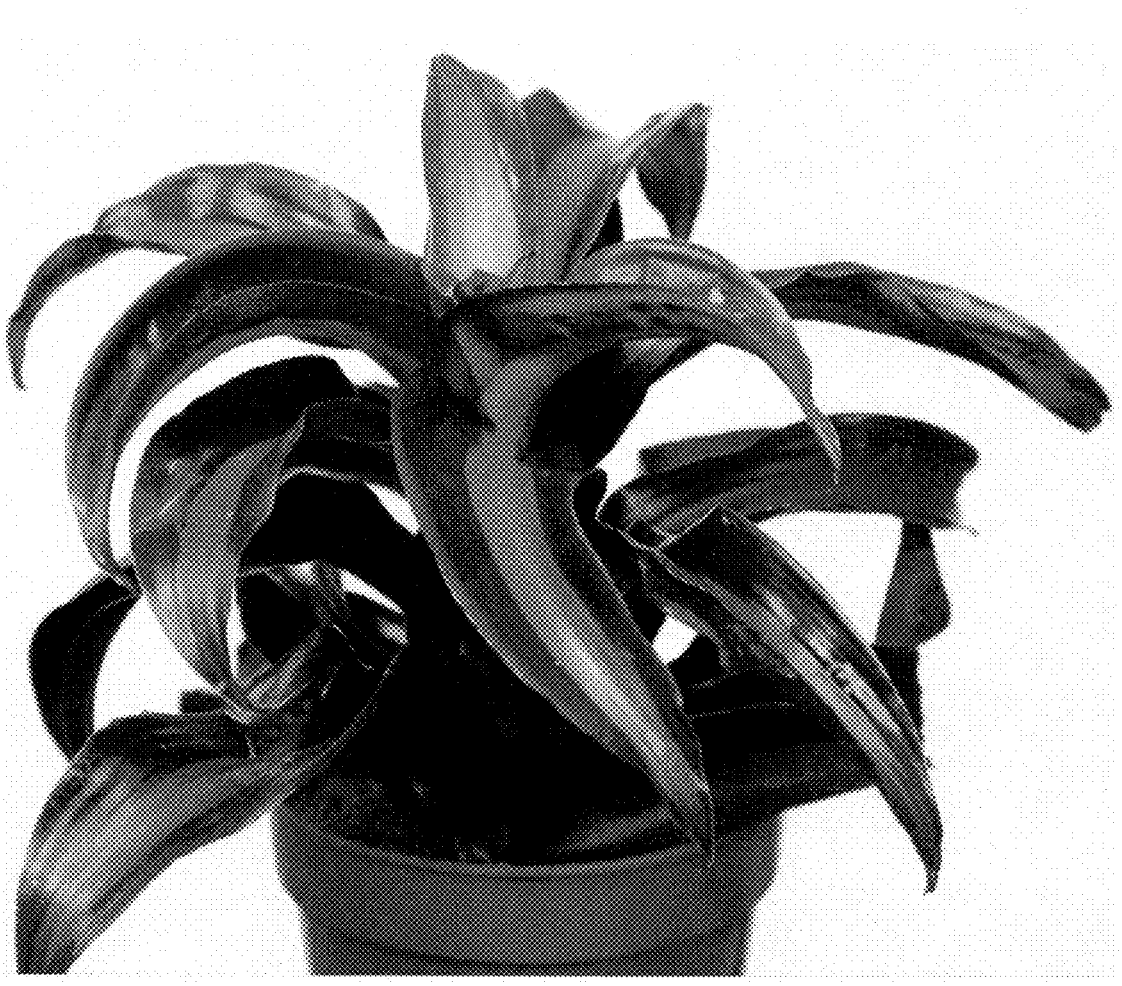
FIG. 1 illustrates, as nearly true as it is reasonably possible to make the same in color photographs of this type, an exemplary plant of 'DRAHUR01' grown in Honselersdijk, the Netherlands. This plant, grown in a 12 cm nursery container, is approximately 16 weeks old from a rooted young plant.
Figure 2:
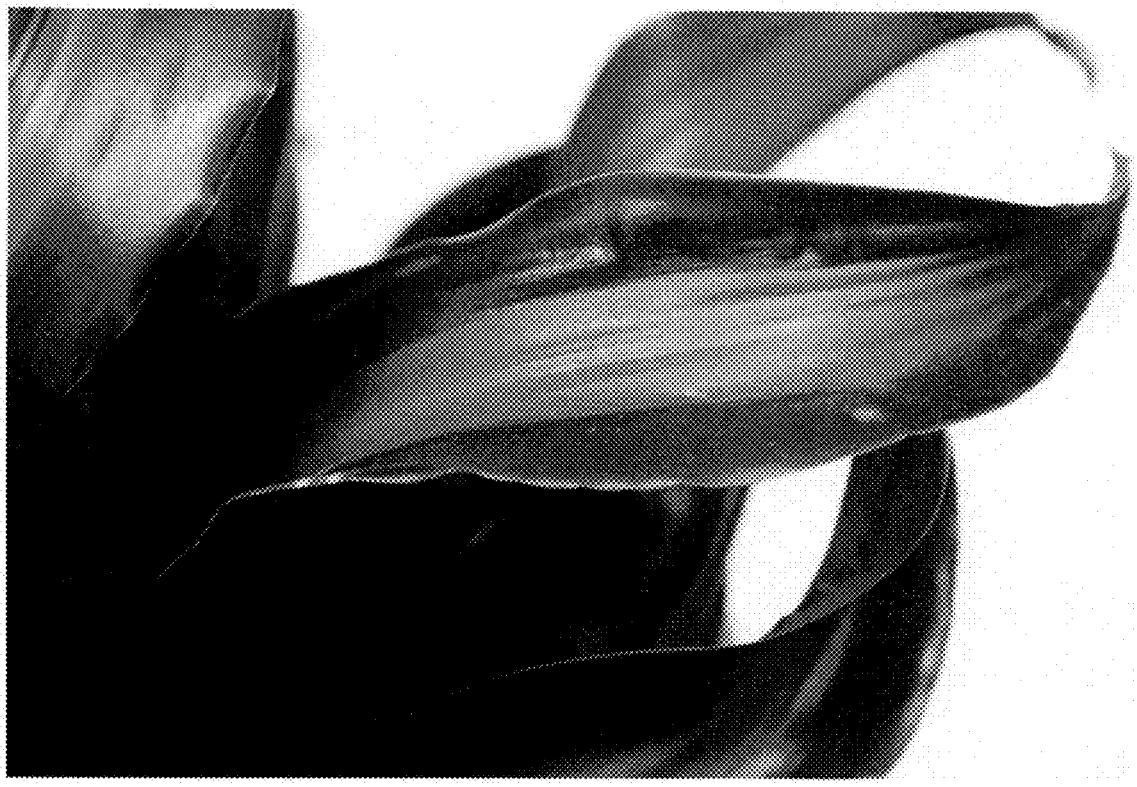
FIG. 2 illustrates, as nearly true as it is reasonably possible to make the same in color photographs of this type, the typical foliage of 'DRAHUR01'.

The following observations and measurements, made in March of 2024, describe averages from a sample set of six specimens of 16-week-old 'DRAHUR01' plants grown in 12 cm nursery pots in Heerhugowaard, the Netherlands. Plants were produced using conventional greenhouse production protocols for *Dracaena* sp. which consisted of growing under shade cloth, regular overhead irrigation, and chemical control of thrips insects. No photoperiodic treatments or artificial light was given to the plants.

Those skilled in the art will appreciate that certain characteristics will vary with older or, conversely, with younger plants. 'DRAHUR01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (Sixth Edition).

A botanical description of 'DRAHUR01' and comparisons with the parent plant and most similar commercial Dracaena cultivar known to the inventor are provided below.

Plant Description:

*Growth habit*.—Compact evergreen perennial with foliage born on a short, unbranched stem.

*Plant profile*.—Flattened globular.

*Average height from base to top of foliage*.—17.8 cm.

*Average width*.—Average of 28.5 cm.

*Plant Vigor*.—Moderately vigorous.

*Propagation Details*.—Asexual propagation is accomplished by stem cuttings.

*Time to initiate roots*.—Approximately 30 days are required to initiate roots at 20 degrees Celsius.

*Time to produce a marketable* 12 *cm potted plant*.—Approximately 12 to 16 weeks.

*Disease and pest resistance or susceptibility*.—Neither tolerance nor resistance to normal diseases and pests of *Dracaena* fragrans have been observed.

*Environmental tolerances*.—Adapt to USDA Hardiness Zones 10 through 12 and temperatures as high as 40 degrees Celsius; moderate tolerance to rain and wind.

Root System:

*General*.—Fibrous; freely branched and moderately dense rooting.

*Distribution in the soil profile*.—Shallow to moderately deep.

*Texture*.—Smooth; glabrous.

*Color*.—Greyed-orange, RHS N170A.

Stems:

*Branching characteristics*.—Not freely branched in nature; develops lateral branches only when manipulated by man by way of pruning. Naturally produces one main stem arising from the plant's base.

*Attitude*.—Near vertical, averaging at an angle of 0-degrees from vertical.

*Strength*.—Very strong.

*Length*.—10.2 cm.

*Diameter*.—Average 1.3 cm.

*Internode length*.—Average 1.2 cm.

*Stem texture*.—Glabrous; smooth.

*Stem luster*.—Very slightly glossy.

*Color, developing stems*.—Yellow-green, nearest to RHS 145B.

*Color, mature stems*.—Yellow-green, nearest to a blend of RHS 145B and 146D.

*Color at the internodes*.—Yellow-green, nearest to RHS 146D.

Foliage:

*Arrangement*.—Alternate; spiraled.

*Attachment*.—Sheathed.

*Division*.—Simple.

*Attitude*.—Foliage is slightly relaxed outwardly at an average angle of 50-degrees, becoming more outwardly sloped and downturned.

*Number of leaves per lateral branch*.—22.

Lamina:

*Dimensions*.—18.4 cm long and 4.8 cm wide, on average.

*Shape*.—Lorate.

*Aspect*.—Slightly concave with the distalmost portion on the lamina pointing downward at an average angle of minus-40 degrees to the rest of the lamina. The lamina also exhibits a slight longitudinal twist, giving the foliage a slightly spiraled appearance.

*Apex*.—Acute with a short, soft but pointed tip.

*Base*.—Sheathed.

*Sheath*.—Length — 2.0 cm. Width — 3.2 cm. Color, adaxial surface — Greyed-green, nearest to RHS 193C, and transitioning to a darker shade of greyed-green towards the margins, nearest to a combination of RHS 191B and 193B; very narrowly margined with a translucent greyed-green, nearest to a mixture of RHS 193A and 193B. Color, abaxial surface — Green, nearest to RHS 137B, and transitioning to a lighter shade of green towards the margins, nearest to RHS 137C; very narrowly margined with a translucent greyed-green, nearest to a mixture of RHS 193A and 193B.

*Margin*.—Entire; light, coarse undulation.

*Texture and luster of adaxial surface*.—Smooth, glabrous and moderately glossy.

*Texture and luster of abaxial surface*.—Smooth, glabrous, and moderately glossy.

*Color*.—Juvenile foliage, adaxial surface — Green to yellow-green, nearest to a blend of RHS 143A and 146A, with broad longitudinal stripes covering approximately one-third of the central portion of the lamina that are colored with a combination of a lighter shade of green and yellow-green, nearest to RHS 143B and 144A; very narrowly margined with a translucent greyed-green, nearest to RHS 192C. Juvenile foliage, abaxial surface — Green, nearest to a blend of RHS 137B and 143A, broadly axially striped near the midrib, colored yellow-green, nearest to 144A; margins narrowly edged translucent greyed-green, nearest to 192C. Mature foliage, adaxial surface — Green to greyed-green, nearest to a blend of RHS 139A and N189A, broadly axially striped near the midrib, colored yellow-green nearest to a blend of 137A and 137B; margins narrowly edged translucent greyed-green nearest to 192C. Mature foliage, abaxial surface — Green, nearest to RHS NN137A, broadly axially striped green along the midrib, nearest to 137B and 137C; margins narrowly edged translucent greyed-green, nearest to 192C.

*Venation*.—Pattern — Parallel. Juvenile color, adaxial surface — The main vein is colored yellow-green, nearest to a mixture of RHS 144A and 144B. All other veins are indistinguishable from the surrounding foliage. Juvenile color, abaxial surface — The main vein is colored yellow-green, nearest to a mixture of RHS 144A and 146B. All other veins are indistinguishable from the surrounding foliage. Mature color, adaxial surface — The main vein is colored green, nearest to a mixture of RHS 137C and 137D. All other veins are indistinguishable from the surrounding foliage. Mature color, abaxial surface — The main vein is green, nearest to RHS 138A. All other veins are indistinguishable from the surrounding foliag.

Inflorescence: To date, flowering has not been observed.

Flower buds: To date, flowering has not been observed.

Flower: To date, flowering has not been observed.

Reproductive Organs: To date, flowering has not been observed.

Seed and Fruit: To date, flowering has not been observed.

Comparisons with the parent plant: Plants of the new cultivar 'DRAHUR01' may be distinguished from its parent, *Dracaena fragrans* 'Kanzi' plant (U.S. Plant Pat. No. 12,691), by the characteristics described in Table 1.

TABLE 1

| Characteristic | 'DRAHUR01' | 'Kanzi' |
|---|---|---|
| General coloration of the mature foliage. | Centered with light yellow-green and broadly margined with dark green to greyed-green. | Centered dark green with fine near-white to very light greyed-green striations, bordered on either side by a larger, prominent white longitudinal stripe, and broadly margined with a relatively light shade of yellow-green. |

TABLE 1-continued

| Characteristic | 'DRAHUR01' | 'Kanzi' |
|---|---|---|
| Lamina aspect. | Slightly concave, curled downward distally, and spiraled. | Moderately concave, curled downward distally, and more strongly spiralled. |

Plants of the new cultivar 'DRAHUR01' may be distinguished from the closest known commercial comparator, *Dracaena fragrans* 'Dradorco' (U.S. Pat. No. 27,785), by the characteristics described in Table 2.

TABLE 2

| Characteristic | 'DRAHUR01' | 'Dradorco' |
|---|---|---|
| Foliage attitude. | More relaxed than 'Dradorco'. | More upright than 'DRAHUR01'. |
| Abundance of foliage. | Less abundant than 'Dradorco'. | More abundant than 'DRAHUR01'. |
| General coloration of the mature foliage. | Centered with light yellow-green and broadly margined with dark green to greyed-green. | Centered dark green and broadly margined with light yellow-green. |

That which is claimed is:

1. A new and distinct cultivar of *Dracaena* plant named 'DRAHUR01', substantially as described and illustrated herein.

* * * * *